United States Patent
Majeed et al.

(10) Patent No.: US 11,413,318 B2
(45) Date of Patent: Aug. 16, 2022

(54) COMPOSITIONS AND METHODS FOR MANAGEMENT OF ATROPHIC GASTRITIS AND COLITIS

(71) Applicants: Muhammed Majeed, Bangalore (IN); Kalyanam Nagabhushanam, East Windsor, NJ (US); Sarang Bani, Bangalore (IN); Anjali Pandey, Bangalore (IN); Shaheen Majeed, Springville, UT (US)

(72) Inventors: Muhammed Majeed, Bangalore (IN); Kalyanam Nagabhushanam, East Windsor, NJ (US); Sarang Bani, Bangalore (IN); Anjali Pandey, Bangalore (IN); Shaheen Majeed, Springville, UT (US)

(73) Assignee: SAMI-SABINSA GROUP LIMITED, Bangalore (IN)

( * ) Notice: Subject to any disclaimer, the term of this patent is extended or adjusted under 35 U.S.C. 154(b) by 0 days.

(21) Appl. No.: 16/903,989

(22) Filed: Jun. 17, 2020

(65) Prior Publication Data

US 2020/0316143 A1    Oct. 8, 2020

Related U.S. Application Data

(63) Continuation-in-part of application No. 16/001,096, filed on Jun. 6, 2018, now Pat. No. 10,792,295.

(60) Provisional application No. 62/516,066, filed on Jun. 6, 2017.

(51) Int. Cl.
    *A61K 35/742*    (2015.01)
    *A61P 1/00*      (2006.01)
    *A61K 31/352*    (2006.01)

(52) U.S. Cl.
    CPC .......... *A61K 35/742* (2013.01); *A61K 31/352* (2013.01); *A61P 1/00* (2018.01)

(58) Field of Classification Search
    CPC ........ A61K 35/742; A61K 31/352; A61P 1/00
    USPC ...................................................... 424/93.46
    See application file for complete search history.

(56) References Cited

U.S. PATENT DOCUMENTS

2016/0129054 A1* 5/2016 Majeed ............... A61K 35/742
                                                        424/93.46
2017/0326190 A1* 11/2017 Ansell ..................... A23L 19/01
2018/0344754 A1* 12/2018 Majeed ................... A61P 31/04

OTHER PUBLICATIONS

Majeed et al., A Double-Blind, Placebo-Controlled, Parallel Study Evaluating the Safety of Bacillus coagulans MTCC 5856 in Healthy Individuals, Journal of Clinical Toxicology, vol. 6, Iss. 1, (2016), pp. 1-9.*

* cited by examiner

*Primary Examiner* — Jennifer M. H. Tichy (57) ABSTRACT

The present invention discloses a method for therapeutic management of atrophic gastritis and colitis using a composition comprising *Bacillus coagulans* MTCC 5856 individually or in combination with anthocyanins. The invention further discloses a method for preventing neoplastic transformation of mucosal cells in gastro-intestinal tract and improving gut barrier function in mammals using a composition comprising *Bacillus coagulans* MTCC 5856 individually or in combination with anthocyanins.

7 Claims, 8 Drawing Sheets
(6 of 8 Drawing Sheet(s) Filed in Color)

COMPOSITIONS AND METHODS FOR MANAGEMENT OF ATROPHIC GASTRITIS AND COLITIS

CROSS REFERENCE TO RELATED APPLICATIONS

This is a continuation-in-part application of U.S. application Ser. No. 16/001,096 filed on 6 Jun. 2018, which in turn claims priority from U.S. provisional application No. 62/516,066, filed on 6 Jun. 2017, the details of which are incorporated herein by reference.

FIELD OF INVENTION

The present invention in general relates to therapeutic interventions for atrophic gastritis and colitis. More specifically, the present invention pertains to a method of therapeutic management for atrophic gastritis and colitis using effective amounts of composition comprising combination of anthocyanins and *Bacillus coagulans* MTCC 5856. Still more specifically, the invention pertains to a method of preventing the progression of atrophic gastritis and colitis to gastric and colorectal carcinoma by improving the mucosal barrier function using a composition comprising anthocyanins and *Bacillus coagulans* MTCC 5856.

BACKGROUND OF INVENTION

Atrophic gastritis is a histopathologic condition characterized by chronic inflammation of the gastric mucosa with loss of the gastric glandular cells and replacement by intestinal-type epithelium, pyloric-type glands, and fibrous tissue. Atrophy of the gastric mucosa occurs at the endpoint of chronic processes, such as chronic gastritis associated with *Helicobacter pylori* infection, other unidentified environmental factors, and autoimmunity directed against gastric glandular cells [Crafa P, Russo M, Miraglia C, et al. From Sidney to OLGA: an overview of atrophic gastritis. Acta Biomed. 2018 Dec. 17. 89(8-S):93-9]. Management of atrophic gastritis is cardinal as any further progression of the pathological condition in patients makes them prone to cancer (gastric adenocarcinoma). Further, the collapse of mucosal barrier leads to the progression to cancer (Yong Shin et al., (2019) Chronic atrophic gastritis and intestinal metaplasia surrounding diffuse-type gastric cancer: Are they just bystanders in the process of carcinogenesis?, PLoS One, 14(12): e0226427). Thus, the neoplastic transformation of gastric mucosa is a point of no return which further requires more rigorous course of treatment. It is hence imperative to prevent the neoplastic transformation by effectively managing the pathological condition of atrophic gastritis.

Similarly, Colitis is a chronic digestive disease characterized by inflammation of the inner lining of the colon. Infection, loss of blood supply in the colon, Inflammatory Bowel Disease (IBD) and invasion of the colon wall with collagen or white blood cells are all possible causes of an inflamed colon. Colitis-associated colorectal cancer (CA-CRC) is the cause of death in 10%-15% of inflammatory bowel disease (IBD) patients. CA-CRC results from the accumulation of mutations in intestinal epithelial cells and progresses through a well-characterized inflammation to dysplasia to carcinoma sequence (Lauren Van Der Kraak, Philippe Gros, and Nicole Beauchemin, "Colitis-associated colon cancer: Is it in your genes?", World J Gastroenterol. 2015 Nov. 7; 21(41): 11688-11699] just as noted for atrophic gastritis. Thus, inflammation and loss in barrier function drive the pathophysiology of gastritis and colitis induced cancer.

Probiotics have been reported to prevent and delay the neoplastic transformation of gastric mucosa (Russo et al., "Probiotics against neoplastic transformation of gastric mucosa: Effects on cell proliferation and polyamine metabolism", World J Gastroenterol. 2014 Oct. 7; 20(37): 13258-13272). The most common probiotics, Lactobacilli and *Bifidobacterium* are administered to prevent gastritis and colitis induce carcinoma. However, it is common technical knowledge that biological effect of probiotics are strain specific and one particular effect cannot be generalized to all strains and species of probiotics (Probiotics: In Depth/ NCCIH, U.S. Department of Health and Human Services, National Institutes of Health). The present invention discloses the therapeutic effects of *Bacillus coagulans* MTCC 5856 in managing atrophic gastritis and colitis.

In a previous study, the inventors validated that *Bacillus coagulans* MTCC 5856 prevented the growth of *Helicobacter pylori* in-vitro (Majeed et al., U.S. application Ser. No. 16/001,096). However, PHOSITA would understand that it is pertinent to a derive a correlation between in-vitro and in-vivo studies before reaching a comprehensive judgement (decision) on a molecule's/composition's biological activity. The present invention discloses the effect of *Bacillus coagulans* MTCC 5856 in diseases caused by *Helicobacter pylori* such as atrophic gastritis.

U.S. Pat. No. 9,579,352 discloses the effect of *Bacillus coagulans* MTCC 5856 in reducing the symptoms of inflammatory bowel syndrome when administered along with Domperidone, Esomeprazole and Metronidazole. The stand alone effect of *Bacillus coagulans*MTCC 5856 in mitigating the effects of inflammatory bowel syndrome was also evaluated (U.S. Ser. No. 10/166,261). However, the ability of *Bacillus coagulans* MTCC 5856 in improving gut barrier function and preventing the neoplastic transformation of gastric mucosa was not reported.

Anthocyanins are one class of flavanoid compounds, which are widely distributed plant polyphenols. They occur in all tissues of higher plants, including leaves, stems, roots, flowers, and fruits. Anthocyanins are 3-glucosides and sambubiosides of anthocyanidins which include Aurantinidin, Cyanidin, Delphinidin, Europinidin, Pelargonidin, Malvidin, Peonidin, Petunidin and Rosinidin. Some of the common anthocyanin pigments include Cyanidin-3-glucoside, Cyanidin-3-sambubioside, Delphinidin-3-sambubioside, Peonidin-3-glucoside, Peonidin-3-sambubioside etc. There is considerable evidence that dietary anthocyanin pigments have preventative and therapeutic roles in a number of human diseases. Anthocyanins are known to improve intestinal barrier function (Valdez et al., "Anthocyanins and intestinal barrier function: a review". Journal of Food Bioactives (2019); 5:18-30. https://doi.org/10.31665/ JFB.2019.5175). However, a person of skill in the art will understand that the effect produced by anthocyanins in reducing inflammatory conditions related to gastritis and colitis in combination with *Bacillus coagulans* MTCC 5856 will be different and is non obvious. The present invention discloses the ability of *Bacillus coagulans* MTCC 5856 individually and in combination with anthocyanins, in improving gut mucosal barrier function and preventing the neoplastic transformation of gut mucosal cells which was previously not evaluated.

The principle objective of the present invention is to provide therapeutic methods for both atrophic gastritis and colitis using a composition comprising *Bacillus coagulans* MTCC 5856 individually or in combination with anthocyanins.

It is another objective of the invention to disclose a method of preventing neoplastic transformation of gastric mucosa in inflammatory conditions of the gut like atrophic gastritis and colitis by improving gut barrier function using a composition comprising *Bacillus coagulans* MTCC 5856 individually or in combination with anthocyanins.

The present invention fulfills the aforesaid objectives and provides further related advantages.

DEPOSIT OF BIOLOGICAL MATERIAL

The deposit of biological material *Bacillus coagulans* SBC37-01 bearing accession number MTCC 5856, mentioned in the instant application has been made on 19 Sep. 2013 at Microbial Type Culture Collection & Gene Bank (MTCC), CSIR-Institute of Microbial Technology, Sector 39-A, Chandigarh-160036, India.

SUMMARY OF THE INVENTION

In a preferred embodiment the present invention relates to a method of therapeutic management of atrophic gastritis in mammals, said method comprising step of administering effective amount of a composition comprising *Bacillus coagulans* MTCC 5856 individually or in combination with 5%-10% w/w anthocyanins, to mammal in need of therapy for atrophic gastritis.

In another preferred embodiment, the invention further discloses a method of therapeutic management of colitis in mammals, said method comprising step of administering effective amount of a composition comprising *Bacillus coagulans* MTCC 5856 individually or in combination with 5%-10% w/w anthocyanins, to mammal in need of therapy for colitis.

In another most preferred embodiment, the present invention relates to a method of preventing neoplastic transformation of mucosal cells in the gastrointestinal tract in inflammatory conditions of gastritis and colitis in mammals, said method comprising step of administering effective amount of a composition comprising *Bacillus coagulans* MTCC 5856 individually or in combination with 5%-10% w/w anthocyanins, to mammals in need of such therapy, to bring about an effect of restoring normal architecture of mucosa with intact epithelial cells.

Other features and advantages of the present invention will become apparent from the following more detailed description, taken in conjunction with the accompanying drawings, which illustrate, by way of example, the principle of the invention.

BRIEF DESCRIPTION OF THE DRAWINGS

The patent or application file contains at least one drawing executed in color. Copies of this patent or patent application publication with color drawing(s) will be provided by the office upon request and payment of the necessary fee.

DETAILED DESCRIPTION OF THE MOST PREFERRED EMBODIMENT

In the most preferred embodiment, the present invention relates to a method of therapeutic management of atrophic gastritis in mammals, said method comprising step of administering effective amount of a composition comprising *Bacillus coagulans* MTCC 5856 individually or in combination with 5%-10% w/w anthocyanins, to mammal in need of therapy for atrophic gastritis. In a related embodiment, the therapeutic effect is improvement in gut barrier function by restoration of normal architecture of gastric mucosa with intact gastric epithelial cells. In another related embodiment, the therapeutic effect is reduction in inflammatory markers selected from the group consisting of IL-17A, IL-1β, and IL-6. In another related embodiment, the therapeutic effect is reduction in lipid peroxidation and oxidative stress. In yet another related embodiment, the therapeutic effect is reduction in elevated levels of enzyme myeloperoxidase. In another related embodiment, the effective amount is 50 mg/kg bodyweight of anthocyanins and 150 mg/kg bodyweight of *Bacillus coagulans* MTCC 5856. In another related embodiment, the anthocyanins are glucosides and sambubiosides of anthocyanidins selected from the group consisting of Aurantinidin, Cyanidin, Delphinidin, Europinidin, Pelargonidin, Malvidin, Peonidin, Petunidin and Rosinidin. In specific embodiment, the mammal is human.

In the most preferred embodiment, the present invention relates to a method of therapeutic management of colitis in mammals, said method comprising step of administering effective amount of a composition comprising *Bacillus coagulans* MTCC 5856 individually or in combination with 5%-10% w/w anthocyanins, to mammal in need of therapy for colitis. In a related embodiment, the therapeutic effect is improvement in mucosal barrier function by restoration of normal architecture of mucosal cells in colon with intact lining of simple columnar epithelial cells. In another related embodiment, the therapeutic effect is reduction in the expression of Lipin 1. In another related embodiment, the therapeutic effect is reduction in lipid peroxidation and oxidative stress. In yet another related embodiment, the therapeutic effect is increase in prostaglandin E2 levels. In another related embodiment, the effective amount is 50 mg/kg bodyweight of anthocyanins and 150 mg/kg bodyweight of *Bacillus coagulans* MTCC 5856. In another related embodiment, the anthocyanins are glucosides and sambubiosides of anthocyanidins selected from the group consisting of Aurantinidin, Cyanidin, Delphinidin, Europinidin, Pelargonidin, Malvidin, Peonidin, Petunidin and Rosinidin. In specific embodiment, the mammal is human.

In another most preferred embodiment, the present invention relates to a method of preventing neoplastic transformation of mucosal cells in the gastrointestinal tract in inflammatory conditions in mammals, said method comprising step of administering effective amount of a composition comprising *Bacillus coagulans* MTCC 5856 individually or in combination with 5%-10% w/w anthocyanins, to mammals in need of such therapy, to bring about an effect of restoring normal architecture of mucosa with intact epithelial cells. In a related embodiment, the inflammatory conditions are selected from the group consisting of atrophic gastritis and colitis. In another related embodiment, the effective amount is 50 mg/kg bodyweight of anthocyanins and 150 mg/kg bodyweight of *Bacillus coagulans* MTCC 5856. In another related embodiment, the anthocyanins are glucosides and sambubiosides of anthocyanidins selected from the group consisting of Aurantinidin, Cyanidin, Delphinidin, Europinidin, Pelargonidin, Malvidin, Peonidin, Petunidin and Rosinidin. In another related embodiment, the mammal is human.

The most preferred embodiments of the invention are further substantiated through illustrative working examples provided below.

Example 1

Experimental atrophic gastritis was induced in male Wistar rats weighing 200-250 grams as per protocol in Zun et al. Chronic gastritis rat model and role of inducing factors; World J Gastroenterol 2004; 10(21):3212-3214 using,
1. 0.5 g/L ammonia solution as drinking water everyday
2. 2 ml of 600 ml/L alcohol twice in fasting per week
3. 2 mL of 20 mmol/L DOC-Na (deoxycorticosterone acetate) without fasting everyday
4. Intragastric administration of DOC-Na twice a week Experimental colitis was induced in rats by intra-colonic administration of 4% acetic acid (2 mL) through a lubricated catheter under low-dose ether anesthesia and treatment was started post-colitis induction as per protocol in Xie et al. *Ganoderma lucidum* polysaccharide improves rat DSS-induced colitis by altering cecal microbiota and gene expression of colonic epithelial cells. Food & Nutrition Research 2019, 63: 1559.

The duration of study for both experimentally induced atrophic gastritis and colitis was 12 weeks. The selected doses of the therapeutic composition to be administered to the experimentally induced atrophic gastritis/colitis animal models were as follows.

1. Anthocyanins: 12.5, 25 and 50 mg/kg p.o. The anthocyanins were isolated from *Garcinia indica* by methods known in the art and standardized to contain 5%-10% w/w anthocyanins (Cyanidin 3-Glucoside and Cyanidin 3-Sambubioside).
2. *Bacillus coagulans* MTCC 5856: 150 mg/kg p.o. rat dose
(equivalent to human dose of 2 billion spores)

For the combination groups, the following doses of the therapeutic composition were chosen 1. Anthocyanins+*Bacillus coagulans* MTCC 5856 (12.5+150) mg/kg p.o
2. Anthocyanins+*Bacillus coagulans* MTCC 5856 (25+150) mg/kg p.o
3. Anthocyanins+*Bacillus coagulans* MTCC 5856 (50+150) mg/kg p.o Estimation of Molecular targets: Blood was collected from the retro-orbital plexus of the experimental animals; no anti-coagulant was added to the blood and it was made to stand at room temperature for 1 h. The blood was then centrifuged, and clear serum was separated and stored for analysis. Samples from different groups of animals were prepared for the analysis of cytokines and mediators at the termination of the experiment. IL-6 (inflammatory mediator for atrophic gastritis), Il-1 beta (inflammatory mediator for atrophic gastritis), IL-17A (involved in parietal cell atrophy and metaplasia in atrophic gastritis), glutathione peroxidase (antioxidant) and myeloperoxidase (marker of oxidative stress) were the molecular targets for atrophic gastritis. Lipin-1 (The phosphatidic acid phosphatase lipin-1 facilitates inflammation-driven colon carcinogenesis), prostaglandin E2-PGE2 (involved in mucosal repair in colitis), glutathione reductase (facilitator of oxidative stress) were the molecular targets for colitis. The effect of tested therapeutic compositions to reduce levels of lipid peroxidation were also evaluated for both atrophic gastritis and colitis. All molecular targets were estimated using commercially available kits based on sandwich and competitive ELISA technique according to the manufacturers' instructions. All cytokine concentrations were carried out by means of colorimetric measurement at 450 nm on an ELISA plate reader by interpolation from a standard curve.

Histopathology as per protocol of Sujai Suneetha, 1993. Histopathological Techniques, in Handbook of CMAI Medical Laboratory Technology by Robert H Carman, Christian Medical Association of India. Chapter 24.508-541.

For Gastric atrophy: The stomach was dissected, fixed, and decalcified in 10 percent formic acid for 21 days. The tissue sections (10 µm) were subjected to hematoxylin and eosin (H&E) staining for routine histological examination.

For Colitis: The part of the colon was dissected, fixed, and decalcified in 10 percent formic acid for 21 days. The tissue sections (10 µm) were subjected to hematoxylin and eosin (H&E) staining for routine histological examination.

Results

Molecular Targets for Atrophic Gastritis

Figure 1:
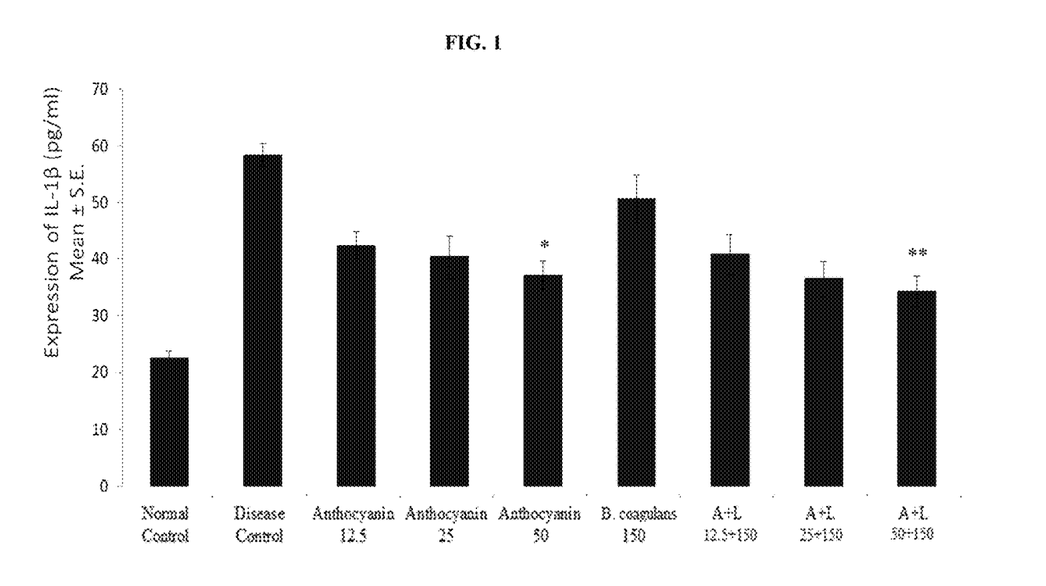
FIG. 1 shows the inhibition of IL-1β or IL-1beta expression by combinations of anthocyanins and *Bacillus coagulans* MTCC 5856 in experimentally induced atrophic gastritis animal models. (A+L: Anthocyanins+*B. coagulans* MTCC 5856; Doses in mg/kg p.o., P value: *<0.01; **<0.001)
Figure 2:
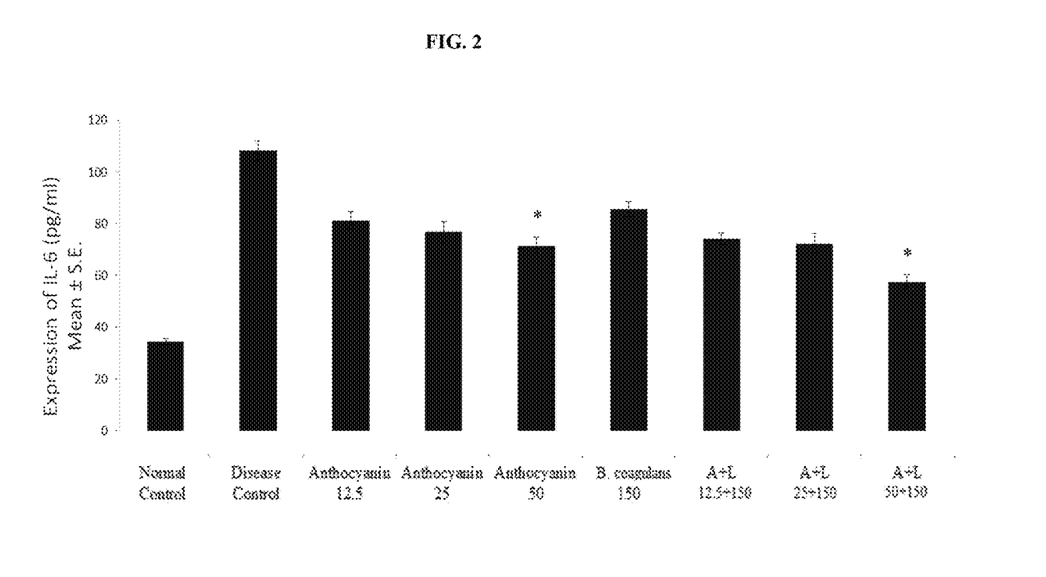
FIG. 2 shows the inhibition of IL-6 expression by combinations of anthocyanins and *Bacillus coagulans* MTCC 5856 in experimentally induced atrophic gastritis animal models. (A+L: Anthocyanins+*B. coagulans* MTCC 5856; Doses in mg/kg p.o., P value: *<0.01; **<0.001)
Figure 3:
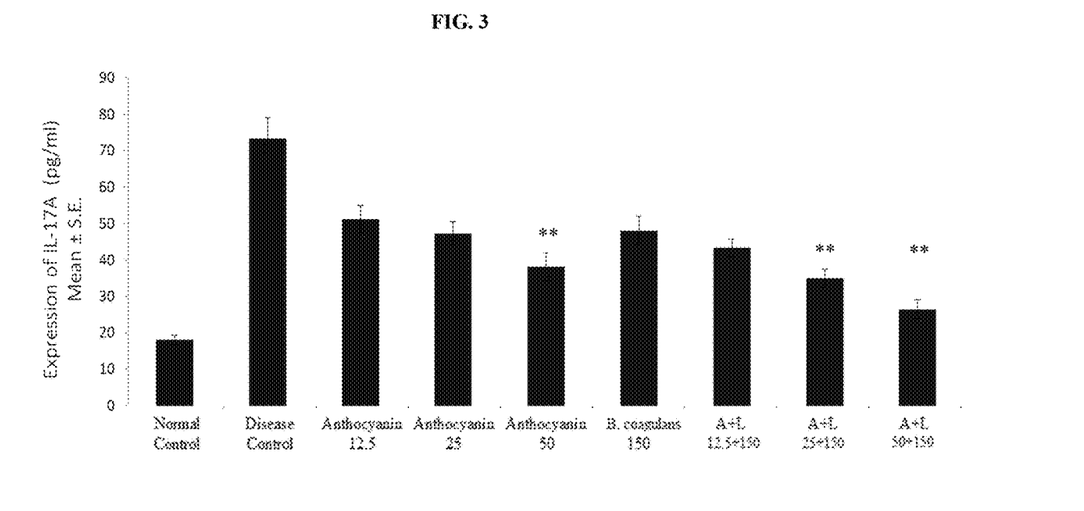
FIG. 3 shows the inhibition of IL-17A expression by combinations of anthocyanins and *Bacillus coagulans* MTCC 5856 in experimentally induced atrophic gastritis animal models. (A+L: Anthocyanins+*B. coagulans* MTCC 5856; Doses in mg/kg p.o., P value: *<0.01; **<0.001)
Figure 4:
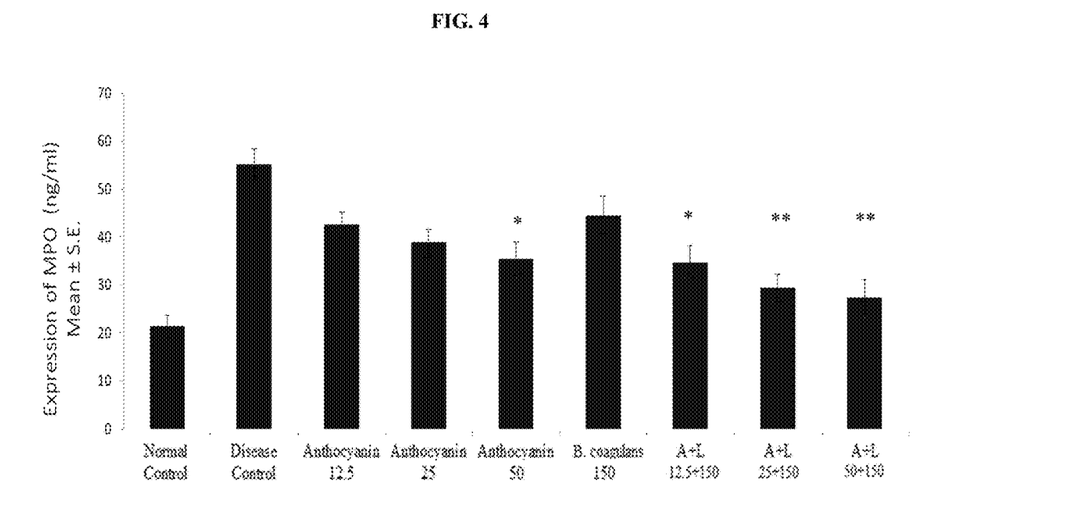
FIG. 4 shows the inhibition of Myeloperoxidase by combinations of anthocyanins and *Bacillus coagulans* MTCC 5856 in experimentally induced atrophic gastritis animal models. (A+L: Anthocyanins+*B. coagulans* MTCC 5856; Doses in mg/kg p.o., P value: *<0.01; **<0.001)
Figure 5A:
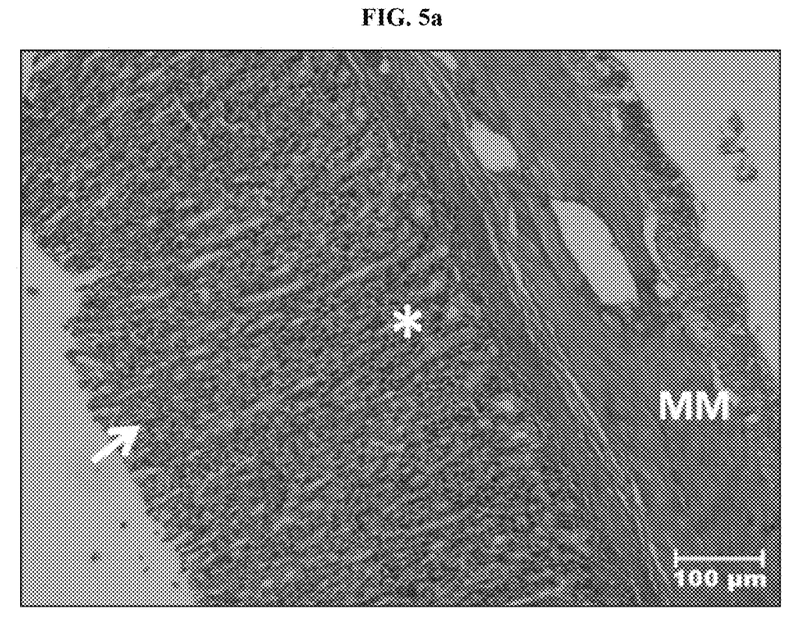
FIG. 5*a* shows the histopathology of normal architecture of gastric mucosa with intact gastric epithelial cells (arrow). The gastric mucosa containing normal secretory gastric glands without any infiltration (asterisk).
Figure 5B:
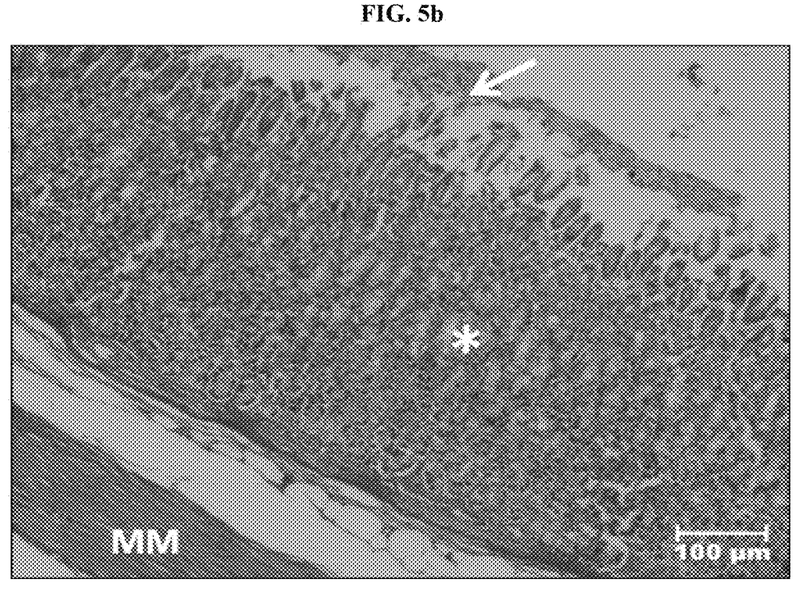
FIG. 5*b* shows the histopathology of atrophic gastritis control. The disruption in normal architecture, coagulative necrosis of gastric mucosa with desquamation of necrotic glandular epithelium and loss of lining gastric epithelial cells (arrow) is evident. The gastric mucosa showing loss of secretory gastric glands and vacuolar degeneration of cells (asterisk), oedema of submucosal layer with separation and arranged in the muscularis mucosa layer (MM) is also evident.
Figure 5C:
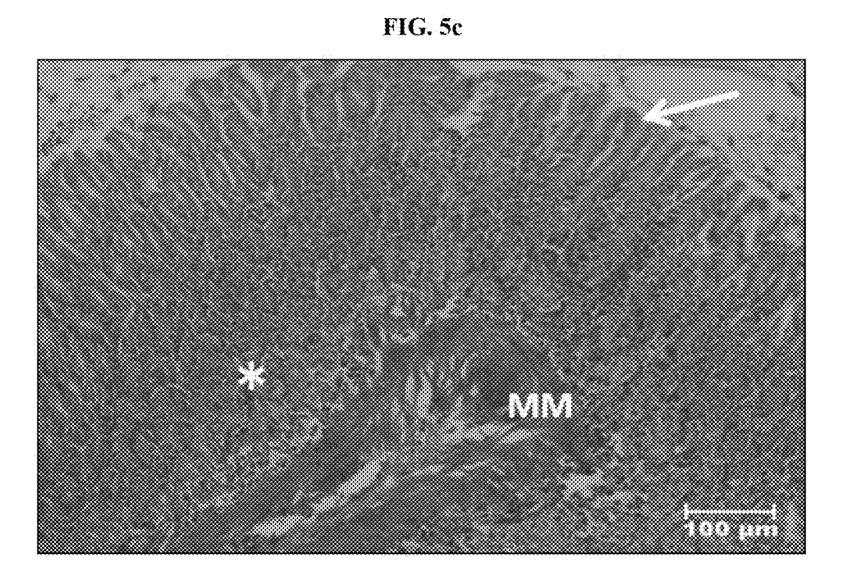
FIG. 5*c* shows the histopathology of experimentally induced atrophic gastritis animal models treated perorally with anthocyanins (dose 50 mg/kg body weight). Stomach shows normal architecture with intact gastric epithelial cells(arrow). The gastric mucosa showing secretory gastric glands (asterisk) arranged on the muscularis mucosa layer.
Figure 5D:
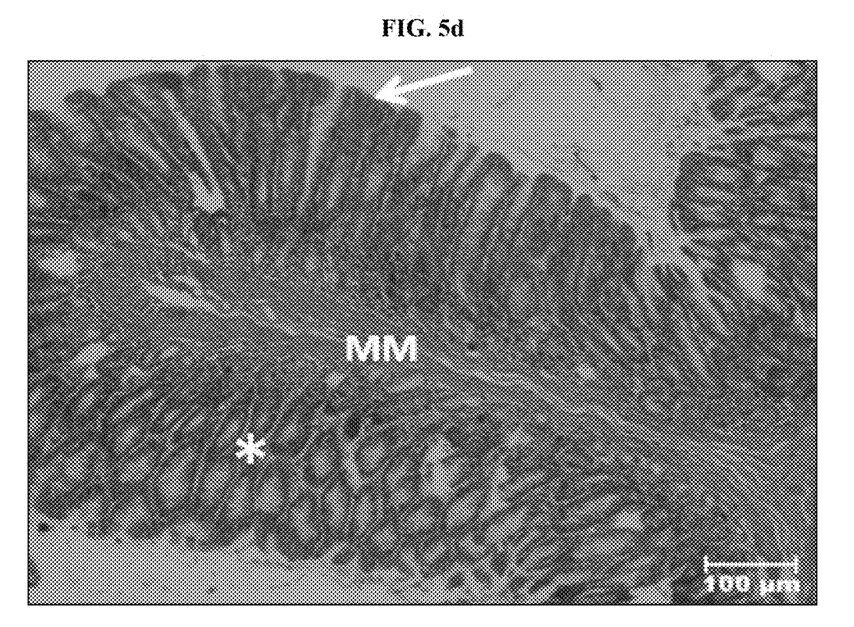
FIG. 5*d* shows the histopathology of experimentally induced atrophic gastritis animal models treated perorally with *Bacillus coagulans* MTCC 5856 (dose 150 mg/kg body weight). Stomach showing normal architecture with intact gastric epithelial cells (arrow) with goblet cell hyperplasia. The gastric mucosa showing secretory gastric glands with secretions (asterisk) arranged on the muscularis mucosa layer (MM).
Figure 5E:
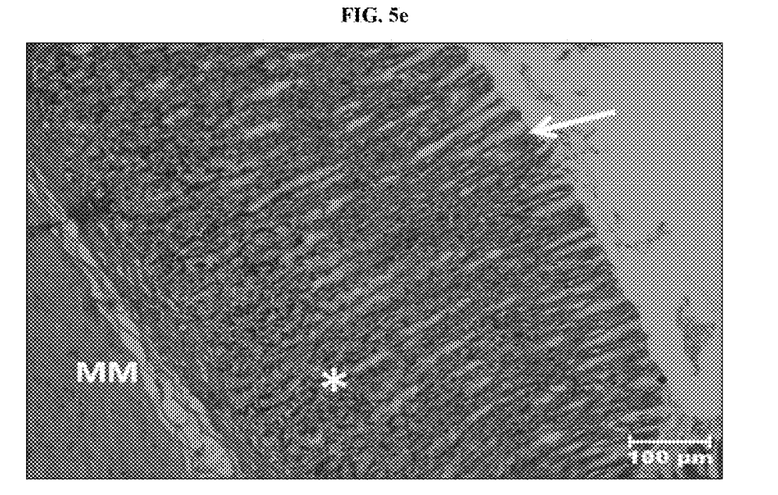
FIG. 5*e* shows the histopathology of experimentally induced atrophic gastritis animal models treated perorally with both anthocyanins (dose 50 mg/kg body weight) and *Bacillus coagulans* MTCC 5856 (dose 150 mg/kg body weight). Stomach showing normal architecture with intact gastric epithelial cells (arrow). The gastric mucosa showing secretory gastric glands with secretions (asterisk) arranged on the muscularis mucosa layer (MM).

1. Anthocyanins+*Bacillus coagulans* MTCC 5856 combination (A+L) at dosage 50+150 mg/kg peroral administration resulted in statistically significant 41.30% inhibition of IL-1β expression (pg/ml) (FIG. 1)
2. Anthocyanins+*Bacillus coagulans* MTCC 5856 combination (A+L) at dosage 50+150 mg/kg peroral administration resulted in statistically significant 46.82% inhibition of IL-6 expression (pg/ml)(FIG. 2)
3. Anthocyanins+*Bacillus coagulans* MTCC 5856 combination (A+L) at dosage 50+150 mg/kg peroral administration resulted in statistically significant inhibition of IL-17 expression (pg/ml)(FIG. 3).
4. Anthocyanins+*Bacillus coagulans* MTCC 5856 combination (A+L) at dosage 50+150 mg/kg peroral administration resulted in statistically significant 50.25% inhibition of myeloperoxidase (FIG. 4).
5. Anthocyanins+*Bacillus coagulans* MTCC 5856 combination (A+L) at dosage 50+150 mg/kg peroral administration resulted in statistically significant inhibition of lipid peroxidation (Table 1).

TABLE 1

Lipid peroxidation in Atrophic gastritis

| Group | Treatment group | LPO (pmol/ml) | % decrease in Activity |
|---|---|---|---|
| I | Normal control (no induction) - vehicle | 44.15 ± 4.20 | — |
| II | Gastric atrophy control | 127.96 ± 5.67 | — |
| III | Anthocyanins (12.5 mg/kg, p.o.) | 121.63 ± 5.50 | 4.95 |
| IV | Anthocyanins (25 mg/kg, p.o.) | 104.67 ± 4.98 | 18.20 |
| V | Anthocyanins (50 mg/kg, p.o.) | 93.98 ± 5.49 | 26.56 |
| VI | *Bacillus coctgulans* MTCC 5856 (150 mg/kg, p.o.) | 90.6 ± 3.87 | 29.19 |
| VII | Anthocyanins (12.5 mg/kg, p.o.) + *Bacillus coagulans* MTCC 5856 (150 mg/kg, p.o.) | 108.26 ± 4.98 | 15.40 |
| VIII | Anthocyanins (25 mg/kg, p.o.) + *Bacillus coagulans* MTCC 5856 (150 mg/kg, p.o.) | 73.35 ± 3.23** | 42.68 |
| IX | Anthocyanins (50 mg/kg, p.o.) + *Bacillus coagulans* MTCC 5856 (150 mg/kg, p.o.) | 68.66 ± 3.67** | 46.34 |

6. Anthocyanins+*Bacillus coagulans* MTCC 5856 combination at dosage 50+150 mg/kg peroral administration resulted in statistically significant increase in glutathione reductase activity (Table 2).

TABLE 2

Glutathione reductase activity in atrophic gastritis

| Group | Treatment group | GSH (µg/l) | % increase in Activity |
|---|---|---|---|
| I | Normal control (no induction) - vehicle | 1056.53 ± 12.80 | — |
| II | Gastric atrophy control | 502.66 ± 5.77 | — |
| III | Anthocyanins (12.5 mg/kg, p.o.) | 607.70 ± 6.90 | 20.90 |
| IV | Anthocyanins (25 mg/kg, p.o.) | 647.23 ± 7.56* | 28.76 |
| V | Anthocyanins (50 mg/kg, p.o.) | 680.40 ± 6.35** | 35.36 |
| VI | *Bacillus coagulans* MTCC 5856 (150 mg/kg, p.o.) | 650.55 ± 7.80* | 79.47 |
| VII | Anthocyanins (12.5 mg/kg, p.o.) + *Bacillus coagulans* MTCC 5856 (150 mg/kg, p.o.) | 645.34 ± 7.23* | 28.38 |
| VIII | Anthocyanins (25 mg/kg, p.o.) + *Bacillus coagulans* MTCC 5856 (150 mg/kg, p.o.) | 702.26 ± 6.21** | 39.71 |
| IX | Anthocyanins (50 mg/kg, p.o.) + *Bacillus coagulans* MTCC 5856 (150 mg/kg, p.o.) | 710.25 ± 7.12** | 41.30 |

Histopathology (FIGS. 5a,5b,5c,5d and 5e) show the progressive restoration of the gastric mucosa containing normal secretory gastric glands without any infiltration from atrophic gastritis pathological manifestation. This confirms that *Bacillus coagulans* MTCC 5856 in combination with anthocyanins restores mucosal barrier function and prevent the neoplastic transformation of gastric epithelial cells.

Molecular Targets for Colitis

Figure 6:
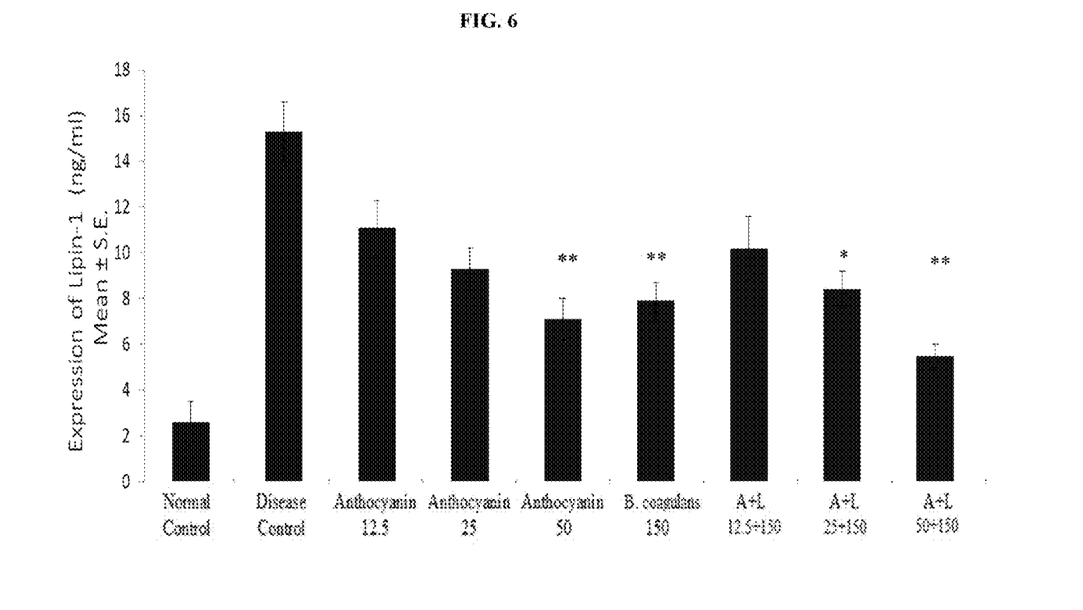
FIG. 6 shows the inhibition of Lipin 1 expression by combinations of anthocyanins and *Bacillus coagulans* MTCC 5856 in experimentally induced colitis animal models. (A+L: Anthocyanins+*B. coagulans* MTCC 5856; Doses in mg/kg p.o., P value: *<0.01; **<0.001)
Figure 7:
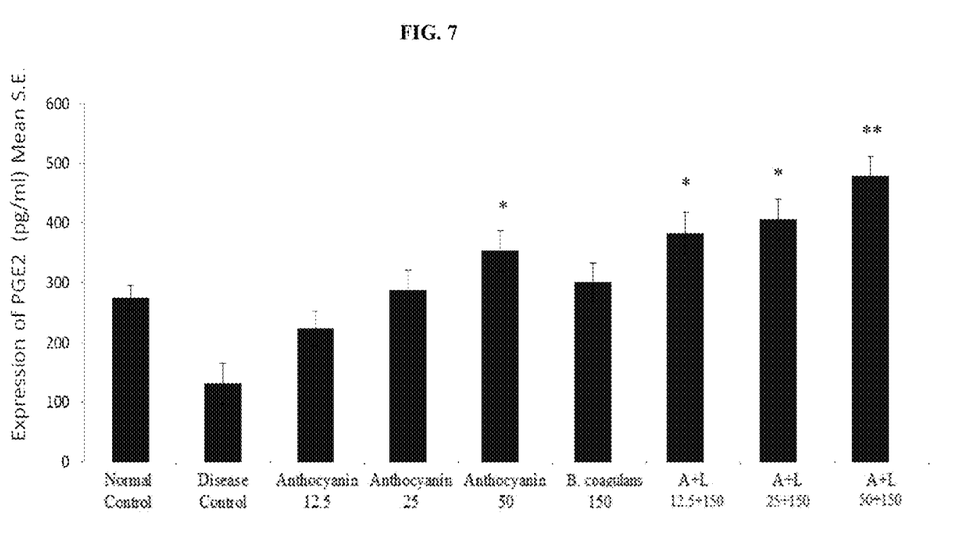
FIG. 7 shows the enhancement in PGE2 expression by combinations of anthocyanins and *Bacillus coagulans* MTCC 5856 in experimentally induced colitis animal models. (A+L: Anthocyanins+*B. coagulans* MTCC 5856; Doses in mg/kg p.o., P value: *<0.01; **<0.001)
Figure 8A:
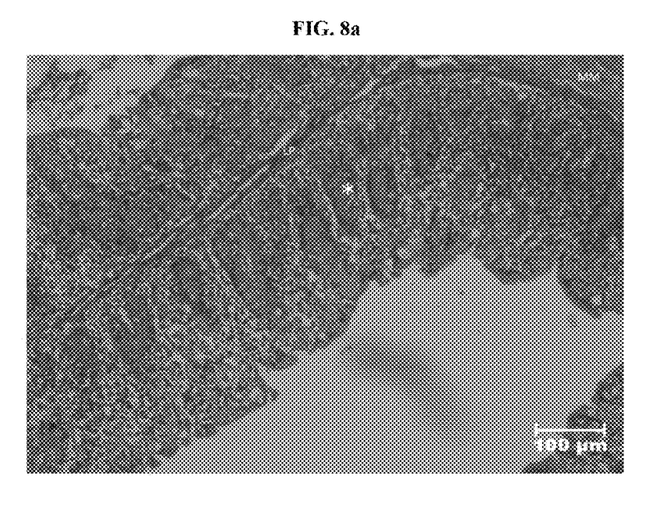
FIG. 8*a* shows the histopathology of a normal colon showing intact lining of simple columnar epithelial cells, numerous goblet cells with normal architecture and intestinal glands containing secretions in the cells with basal nucleus (asterisk), arranged on the lamina propria (LP) which in turn arranged on muscularis mucosa (MM).
Figure 8B:
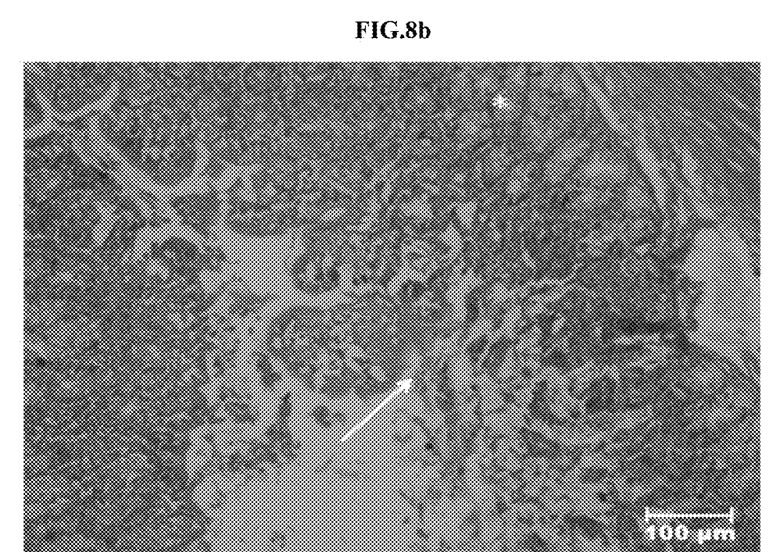
FIG. 8*b* shows histopathology of colitis control (experimentally induced colitis animal model) showing severe loss of lining simple columnar epithelial cells and architecture, necrosis and degeneration of mucosal layer (arrow). The intestinal glands showed increased secretions (asterisk) and severe infiltration of inflammatory cells mainly mono nuclear cells in the sub mucosal layer and tissue debris in the colon lumen.
Figure 8C:
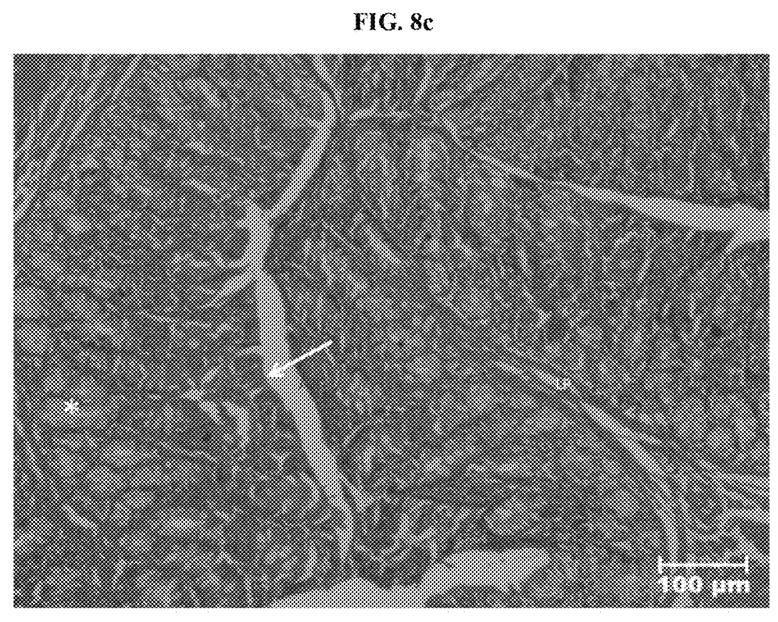
FIG. 8c shows histopathology of colitis control (experimentally induced colitis animal model) treated perorally with Anthocyanins (dose 50 mg/kg body weight) where colon shows intact lining simple columnar epithelial cells with numerous goblet cells and normal architecture of mucosal layer (arrow). The intestinal glands showed columnar epithelial cells with basal nucleus (asterisk) with mild infiltration of mononuclear cells and arranged on the lamina propria (LP), which in turn on the muscularis mucosa layer (MM).
Figure 8D:
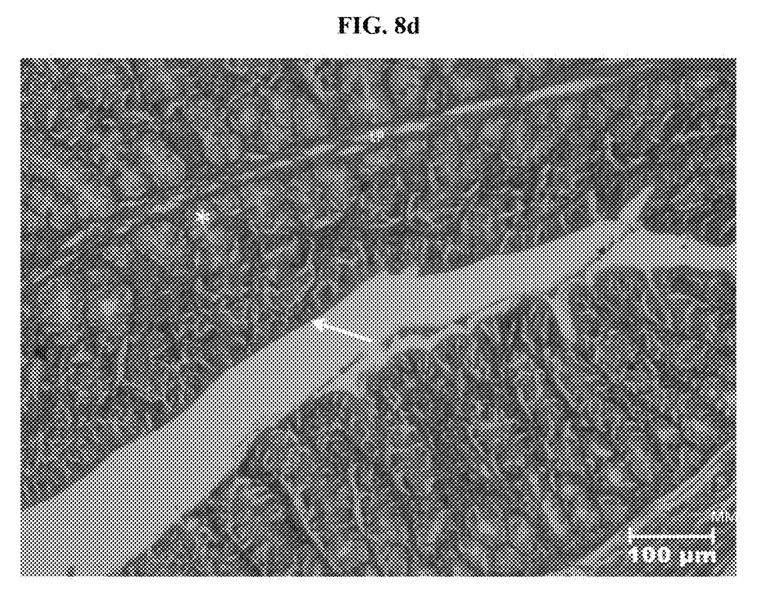
FIG. 8d shows histopathology of colitis control (experimentally induced colitis animal model) treated perorally with *Bacillus coagulans* MTCC 5856 (dose 150 mg/kg body weight) where colon shows intact lining simple columnar epithelial cells and normal architecture of mucosal layer (arrow) with mild infiltration of mononuclear cells in mucosa. The intestinal glands showed columnar epithelial cells with basal nucleus(asterisk) with secretions and arranged on the lamina propria (LP), which in turn on the muscularis mucosa layer (MM).
Figure 8E:
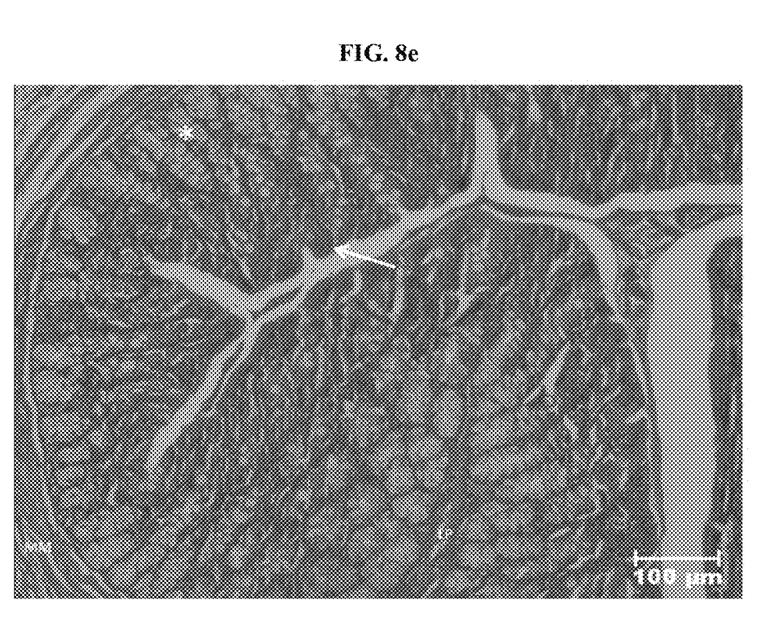
FIG. 8e shows histopathology of colitis control (experimentally induced colitis animal model) treated perorally with both Anthocyanins (dose 50 mg/kg body weight) and *Bacillus coagulans* MTCC 5856 (dose 150 mg/kg body weight), where colon shows intact lining simple columnar epithelial cells and normal architecture of mucosal layer (arrow) with numerous goblet cells. The intestinal glands showed columnar epithelial cells with basal nucleus (asterisk) with secretions and arranged on the lamina propria (LP), which in turn on the muscularis mucosa layer

1. Anthocyanins+*Bacillus coagulans* MTCC 5856 combination at dosage 50+150 mg/kg peroral administration resulted in statistically significant inhibition of Lipin 1 (ng/ml) expression. (FIG. 6)
2. Anthocyanins+*Bacillus coagulans* MTCC 5856 combination at dosage 50+150 mg/kg peroral administration resulted in statistically significant enhancement of PGE2 (ng/ml) expression. (FIG. 7)
3. Anthocyanins+*Bacillus coagulans* MTCC 5856 combination at dosage 50+150 mg/kg peroral administration resulted in statistically significant inhibition of lipid peroxidation (Table 3).

TABLE 3

Lipid Peroxidation in colitis

| Group | Treatment group | LPO (pmol/ml) | % decrease in Activity |
|---|---|---|---|
| I | Normal control (no induction) - vehicle | 23.25 ± 1.20 | — |
| II | Gastric atrophy control | 44.05 ± 2.54 | — |
| III | Anthocyanins (12.5 mg/kg, p.o.) | 36.74 ± 1.55 | 16.59 |
| IV | Anthocyanins (25 mg/kg, p.o.) | 34.86 ± 2.07 | 20.86 |
| V | Anthocyanins (50 mg/kg, p.o.) | 30.27 ± 1.60* | 31.28 |
| VI | *Bacillus coagulans* MTCC 5856 (150 mg/kg, p.o.) | 30.01 ± 1.01* | 31.87 |
| VII | Anthocyanins (12.5 mg/kg, p.o.) + *Bacillus coagulans* MTCC 5856 (150 mg/kg, p.o.) | 29.58 ± 2.04* | 32.85 |
| VIII | Anthocyanins (25 mg/kg, p.o.) + *Bacillus coagulans* MTCC 5856 (150 mg/kg, p.o.) | 29.03 ± 2.12* | 34.10 |
| IX | Anthocyanins (50 mg/kg, p.o.) + *Bacillus coagulans* MTCC 5856 (150 mg/kg, p.o.) | 27.81 ± 1.56* | 36.87 |

4. Anthocyanins+*Bacillus coagulans* MTCC 5856 combination at dosage 50+150 mg/kg peroral administration resulted in statistically significant increase in glutathione reductase activity (Table 4).

TABLE 4

Glutathione reductase levels in colitis

| Group | Treatment group | GSH (µg/l) | % increase in Activity |
|---|---|---|---|
| I | Normal control (no induction) - vehicle | 1007.40 ± 8.28 | — |
| II | Gastric atrophy control | 604.35 ± 6.48 | — |
| III | Anthocyanins (12.5 mg/kg, p.o.) | 696.50 ± 7.58 | 15.25 |
| IV | Anthocyanins (25 mg/kg, p.o.) | 766.95 ± 6.38 | 26.90 |
| V | Anthocyanins (50 mg/kg, p.o.) | 779.90 ± 7.25* | 29.05 |
| VI | *Bacillus coagulans* MTCC 5856 (150 mg/kg, p.o.) | 742.05 ± 7.24 | 22.78 |
| VII | Anthocyanins (12.5 mg/kg, p.o.) + *Bacillus coagulans* MTCC 5856 (150 mg/kg, p.o.) | 730.05 ± 6.16 | 20.80 |
| VIII | Anthocyanins (25 mg/kg, p.o.) + *Bacillus coagulans* MTCC 5856 (150 mg/kg, p.o.) | 768.55 ± 5.89* | 27.17 |
| IX | Anthocyanins (50 mg/kg, p.o.) + *Bacillus coagulans* MTCC 5856 (150 mg/kg, p.o.) | 861.25 ± 6.38** | 42.51 |

Histopathology (FIGS. 8a,8b,8c,8d and 8e) show the progressive restoration of the colon showing intact lining simple columnar epithelial cells and normal architecture of mucosal layer (arrow) with numerous goblet cells from the colitis pathology. The intestinal glands showed columnar epithelial cells with basal nucleus (asterisk) with secretions and arranged on the lamina propria (LP), which in turn on the muscularis mucosa layer (MM). This confirms that *Bacillus coagulans* MTCC 5856 in combination with anthocyanins restores mucosal barrier function and prevent the neoplastic transformation of columnar epithelial cells in colon.

While the invention has been described with reference to a preferred embodiment, it is to be clearly understood by those skilled in the art that the invention is not limited thereto. Rather, the scope of the invention is to be interpreted only in conjunction with the appended claims.

We claim:

1. A method of therapeutic management of atrophic gastritis in mammals, said method comprising a step of administering an effective amount of a composition comprising *Bacillus coagulans* MTCC 5856, to the mammal in need of therapy for atrophic gastritis.

2. The method as in claim 1, wherein therapeutic management of atrophic gastritis is brought about by improving gut barrier function by restoration of normal architecture of gastric mucosa with intact gastric epithelial cells.

3. The method as in claim 1, wherein, therapeutic management of atrophic gastritis is brought about by reducing inflammatory markers selected from the group consisting of IL-17A, IL-1β, and IL-6.

4. The method as in claim 1, wherein therapeutic management of atrophic gastritis is brought about by reducing lipid peroxidation and oxidative stress.

5. The method as in claim 1, wherein therapeutic management of atrophic gastritis is brought about by reducing elevated levels of enzyme myeloperoxidase.

6. The method as in claim 1, wherein the effective amount is 150 mg/kg bodyweight of *Bacillus coagulans* MTCC 5856, equivalent to 2 billion spores.

7. The method as in claim 1, wherein the mammal is human.

* * * * *